US008058465B2

(12) United States Patent
Fukuoka et al.

(10) Patent No.: US 8,058,465 B2
(45) Date of Patent: Nov. 15, 2011

(54) PROCESS FOR INDUSTRIALLY PRODUCING DIALKYL CARBONATE AND DIOL

(75) Inventors: Shinsuke Fukuoka, Tokyo (JP); Hironori Miyaji, Tokyo (JP); Hiroshi Hachiya, Tokyo (JP); Kazuhiko Matsuzaki, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 431 days.

(21) Appl. No.: 11/991,076

(22) PCT Filed: Nov. 17, 2006

(86) PCT No.: PCT/JP2006/323022
§ 371 (c)(1),
(2), (4) Date: Oct. 10, 2008

(87) PCT Pub. No.: WO2007/060894
PCT Pub. Date: May 31, 2007

(65) Prior Publication Data
US 2009/0137833 A1 May 28, 2009

(30) Foreign Application Priority Data
Nov. 25, 2005 (JP) ................. 2005-340193

(51) Int. Cl.
C07C 69/96 (2006.01)
(52) U.S. Cl. ...................................... 558/277
(58) Field of Classification Search .................. 558/277
See application file for complete search history.

(56) References Cited

U.S. PATENT DOCUMENTS

| | | | |
|---|---|---|---|
| 3,642,858 A | 2/1972 | Frevel et al. | |
| 3,803,201 A | 4/1974 | Gilpin et al. | |
| 4,062,884 A | 12/1977 | Romano et al. | |
| 4,181,676 A | 1/1980 | Buysch et al. | |
| 4,307,032 A | 12/1981 | Krimm et al. | |
| 4,661,609 A | 4/1987 | Knifton | |
| 4,691,041 A | 9/1987 | Duranleau et al. | |
| 4,734,518 A | 3/1988 | Knifton | |
| 5,231,212 A | 7/1993 | Buysch et al. | |
| 5,359,118 A | 10/1994 | Wagner et al. | |
| 5,847,189 A | 12/1998 | Tojo et al. | |
| 6,346,638 B1 * | 2/2002 | Tojo et al. | 558/277 |
| 6,479,689 B1 | 11/2002 | Tojo et al. | |
| 7,645,896 B2 | 1/2010 | Tojo et al. | |
| 2008/0221348 A1 | 9/2008 | Fukuoka et al. | |

FOREIGN PATENT DOCUMENTS

| | | |
|---|---|---|
| EP | 0 530 615 A2 | 8/1992 |
| EP | 0 569 812 A1 | 5/1993 |
| EP | 0 889 025 A1 | 1/1999 |
| EP | 1 086 940 A1 | 3/2001 |
| EP | 1 174 406 A1 | 1/2002 |
| EP | 1426086 A1 | 6/2004 |
| EP | 1792890 A1 | 6/2007 |
| EP | 1795523 A1 | 6/2007 |
| EP | 1953131 A1 | 8/2008 |
| EP | 1961721 A1 | 8/2008 |
| EP | 1961722 A1 | 8/2008 |
| EP | 1961723 A1 | 8/2008 |
| EP | 1961731 A1 | 8/2008 |
| EP | 1961732 A1 | 8/2008 |
| EP | 1964829 A1 | 9/2008 |
| EP | 1964831 A1 | 9/2008 |
| EP | 1967242 A1 | 9/2008 |
| EP | 1980548 A1 | 10/2008 |
| GB | 2109265 A | 6/1983 |
| JP | 51-122025 A | 10/1976 |
| JP | 54-48715 A | 4/1979 |
| JP | 54-48716 A | 4/1979 |
| JP | 54-063023 A | 5/1979 |
| JP | 54-148726 A | 11/1979 |
| JP | 63-41432 A | 2/1988 |
| JP | 63-238043 A | 10/1988 |
| JP | 64-31737 A | 2/1989 |
| JP | 04-198141 A | 7/1992 |
| JP | 04-230243 A | 8/1992 |
| JP | 5-213830 A | 8/1993 |
| JP | 6-9507 A | 1/1994 |
| JP | 6-196464 A | 7/1994 |
| JP | 6-228026 A | 8/1994 |
| JP | 7-025830 A | 1/1995 |
| JP | 09-176061 A | 7/1997 |
| JP | 9-183744 A | 7/1997 |
| JP | 09-194435 A | 7/1997 |
| JP | 2000-281630 A | 10/2000 |

(Continued)

OTHER PUBLICATIONS

Chinese Office Action dated Apr. 14, 2011 for Chinese Application No. 200680049253.1.
European Search Report dated Nov. 25, 2010 for European Application No. 06834816.8.
Machine generated translation of JP-6-228026-A dated Aug. 16, 1994.
Musch et al. "Robost PID control for an industrial distillation column" IEEE Control Sytems, 1995, pp. 45-55.
U.S. Office Action for U.S. Appl. No. 11/991,251 dated Jun. 22, 2011.
Supplementary Eurpopean Search Report dated Aug. 5, 2011, for U.S. Appl. No. 06832900.2.

*Primary Examiner* — Rei-tsang Shiao
(74) *Attorney, Agent, or Firm* — Birch, Stewart, Kolasch & Birch, LLP

(57) ABSTRACT

A process for industrially producing dialkyl carbonate and a diol continuously through a reactive distillation system is disclosed. The process includes the steps of taking a cyclic carbonate and an aliphatic monohydric alcohol as starting materials, continuously feeding the starting materials into a continuous multi-stage distillation column in which a catalyst is present, carrying out reaction and distillation simultaneously in the column, continuously withdrawing a low boiling point reaction mixture containing the produced dialkyl carbonate from an upper portion of the column in a gaseous form, and continuously withdrawing a high boiling point reaction mixture containing the diol from a lower portion of the column in a liquid form. According to the present invention, there is provided a specific continuous multi-stage distillation column having a specified structure, and a production process using this continuous multi-stage distillation column.

9 Claims, 1 Drawing Sheet

FOREIGN PATENT DOCUMENTS

| | | | |
|---|---|---|---|
| JP | 2002-308804 A | 10/2002 |
| JP | 2002-371037 A | 12/2002 |
| JP | 2003-119168 A | 4/2003 |
| JP | 2003-300936 A | 10/2003 |
| JP | 2003-342209 A | 12/2003 |
| JP | 2004-131394 A | 4/2004 |
| JP | 2006-182683 A | 7/2006 |
| JP | 2006-199643 A | 8/2006 |
| JP | 2006-206497 A | 8/2006 |
| WO | WO-97/23445 A1 | 7/1997 |
| WO | WO-99/64382 A1 | 12/1999 |
| WO | WO-00/51954 A1 | 9/2000 |
| WO | WO-03/006418 A1 | 1/2003 |
| WO | 03/033450 A1 | 4/2003 |
| WO | WO-2005/123638 A1 | 12/2005 |
| WO | WO-2006/001256 A1 | 1/2006 |

\* cited by examiner

US 8,058,465 B2

PROCESS FOR INDUSTRIALLY PRODUCING DIALKYL CARBONATE AND DIOL

TECHNICAL FIELD

The present invention relates to an industrial process for the production of dialkyl carbonates and diols. More particularly, the present invention relates to a process for industrially producing large amounts of dialkyl carbonates and diols stably for a prolonged period of time through a reactive distillation system of taking a cyclic carbonate and an aliphatic monohydric alcohol as starting materials, continuously feeding the starting materials into a continuous multi-stage distillation column in which a catalyst is present, and carrying out reaction and distillation simultaneously in the column.

BACKGROUND ART

Several processes for the production of dialkyl carbonates and diols from a reaction between a cyclic carbonate and an aliphatic monohydric alcohol have been proposed, but most of these proposals relate to a catalyst. As reaction systems, four systems have been proposed hitherto. These four reaction systems are used in a process for the production of dimethyl carbonate and ethylene glycol from ethylene carbonate and methanol, which is the most typical reaction example.

A first system is a completely batch reaction system in which ethylene carbonate, methanol and a catalyst are put into an autoclave, which is a batch reaction vessel, and reaction is carried out by holding for a predetermined reaction time under an applied temperature at a reaction temperature above the boiling point of methanol (see, for example, Patent Document 1: U.S. Pat. No. 3,642,858, Patent Document 2: Japanese Patent Application Laid-Open No. S54-48715 (corresponding to U.S. Pat. No. 4,181,676), Patent Document 5: Japanese Patent Application Laid-Open No. S54-63023, Patent Document 6: Japanese Patent Application Laid-Open No. S54-148726).

A second system is a system that uses an apparatus in which a distillation column is provided on top of a reaction vessel; ethylene carbonate, methanol and a catalyst are put into the reaction vessel, and reaction is made to proceed by heating to a predetermined temperature. With this system, to make up for methanol distilled off through azeotropy with the produced dimethyl carbonate, methanol is added to the reaction vessel continuously or in batches, but in any event with this system the reaction proceeds only in the reaction vessel, which is batch type, in which the catalyst, ethylene carbonate and methanol are present. The reaction is thus batch type, the reaction being carried out using a large excess of methanol under reflux taking a long time in a range of from 3 to over 20 hours (see, for example, Patent Document 3: Japanese Patent Application Laid-Open No. S51-122025 (corresponding to U.S. Pat. No. 4,062,884), Patent Document 4: Japanese Patent Application Laid-Open No. S54-48716 (corresponding to U.S. Pat. No. 4,307,032), Patent Document 11: U.S. Pat. No. 3,803,201).

A third system is a continuous reaction system in which a mixed solution of ethylene carbonate and methanol is continuously fed into a tubular reactor maintained at a predetermined reaction temperature, and a reaction mixture containing unreacted ethylene carbonate and methanol and dimethyl carbonate and ethylene glycol which are produced is continuously withdrawn in a liquid form from an outlet on the other side. Either of two processes is used depending on the form of the catalyst used. That is, there are a process in which a homogeneous catalyst is used, and is passed through the tubular reactor together with the mixed solution of ethylene carbonate and methanol, and then after the reaction the catalyst is separated out from the reaction mixture (see, for example, Patent Document 7: Japanese Patent Application Laid-Open No. 63-41432 (corresponding to U.S. Pat. No. 4,661,609), Patent Document 10: U.S. Pat. No. 4,734,518), and a process in which a heterogeneous catalyst fixed inside the tubular reactor is used (see, for example, Patent Document 8: Japanese Patent Application Laid-Open No. S63-238043, Patent Document 9: Japanese Patent Application Laid-Open No. S64-31737 (corresponding to U.S. Pat. No. 4,691,041)). The reaction producing dimethyl carbonate and ethylene glycol through reaction between ethylene carbonate and methanol is an equilibrium reaction, and hence with this continuous flow reaction system using a tubular reactor, it is impossible to make the ethylene carbonate conversion higher than the equilibrium conversion determined by the composition ratio put in and the reaction temperature. For example, according to Example 1 in Patent Document 7 (Japanese Patent Application Laid-Open No. S63-41432 (corresponding to U.S. Pat. No. 4,661,609)), for a flow reaction at 130° C. using a starting material put in with a molar ratio of methanol/ethylene carbonate=4/1, the ethylene carbonate conversion is 25%. This means that a large amount of unreacted ethylene carbonate and methanol remaining in the reaction mixture must be separated out, recovered, and recirculated back into the reactor, and in actual fact, with the process of Patent Document 9 (Japanese Patent Application Laid-Open No. S64-31737 (corresponding to U.S. Pat. No. 4,691,041)), much equipment is used for such separation, purification, recovery, and recirculation.

A fourth system is a reactive distillation system first disclosed by the present inventors (see, for example, Patent Document 12: Japanese Patent Application Laid-Open No. H4-198141, Patent Document 13: Japanese Patent Application Laid-Open No. H4-230243, Patent Document 14: Japanese Patent Application Laid-Open No. H9-176061, Patent Document 15: Japanese Patent Application Laid-Open No. H9-183744, Patent Document 16: Japanese Patent Application Laid-Open No. H9-194435, Patent Document 17: International Publication No. WO97/23445 (corresponding to European Patent No. 0889025, U.S. Pat. No. 5,847,189), Patent Document 18: International Publication No. WO99/64382 (corresponding to European Patent No. 1086940, U.S. Pat. No. 6,346,638), Patent Document 19: International Publication No. WO00/51954 (corresponding to European Patent No. 1174406, U.S. Pat. No. 6,479,689), Patent Document 20: Japanese Patent Application Laid-Open No. 2002-3.08804, Patent Document 21: Japanese Patent Application Laid-Open No. 2004-131394), that is a continuous production process in which ethylene carbonate and methanol are each continuously fed into a multi-stage distillation column, and reaction is carried out in the presence of a catalyst in a plurality of stages in the distillation column, while dimethyl carbonate and ethylene glycol which are produced are separated off. Patent applications in which such a reactive distillation system is used have subsequently been filed by other companies (see, for example, Patent Document 22: Japanese Patent Application Laid-Open No. H5-213830 (corresponding to European Patent No. 0530615, U.S. Pat. No. 5,231,212), Patent Document 23: Japanese Patent Application Laid-Open No. H6-9507 (corresponding to European Patent No. 0569812, U.S. Pat. No. 5,359,118), Patent Document 24: Japanese Patent Application Laid-Open No. 2003-119168 (corresponding to International Publication No. WO03/006418), Patent Document 25: Japanese Patent Application Laid-Open No. 2003-300936, Patent Document 26: Japanese Patent Application Laid-Open No. 2003-342209).

In this way, the processes proposed hitherto for producing the dialkyl carbonates and the diols from the cyclic carbonate and the aliphatic monohydric alcohol are the four systems:
(1) a completely batch reaction system;
(2) a batch reaction system using a reaction vessel having a distillation column provided on top thereof;
(3) a flowing liquid reaction system using a tubular reactor; and
(4) a reactive distillation system.

However, there have been problems with these as follows.

In the case of (1) and (3), the upper limit of the cyclic carbonate conversion is determined by the composition put in and the temperature, and hence the reaction cannot be carried out to completion, and thus the conversion is low. Moreover, in the case of (2), to make the cyclic carbonate conversion high, the produced dialkyl carbonate must be distilled off using a very large amount of the aliphatic monohydric alcohol, and a long reaction time is required. In the case of (4), the reaction can be made to proceed with a higher conversion than with (1), (2) or (3). However, processes of (4) proposed hitherto have related to producing the dialkyl carbonate and the diol either in small amounts or for a short period of time, and have not related to carrying out the production on an industrial scale stably for a prolonged period of time. That is, these processes have not attained the object of producing a dialkyl carbonate continuously in a large amount (e.g. not less than 2 ton/hr) stably for a prolonged period of time (e.g. not less than 1000 hours, preferably not less than 3000 hours, more preferably not less than 5000 hours).

For example, the maximum values of the height (H: cm), diameter (D: cm), and number of stages (n) of the reactive distillation column, the produced amount P (kg/hr) of dimethyl carbonate, and the continuous production time T (hr) in examples disclosed for the production of dimethyl carbonate (DMC) and ethylene glycol (EG) from ethylene carbonate and methanol are as in Table 1.

Table 1

TABLE 1

| PATENT DOCUMENT | H: cm | D: cm | NO. STAGES: n | P: kg/hr | T: hr |
|---|---|---|---|---|---|
| 12 | 100 | 2 | 30 | 0.106 | 400 |
| 15 | 160 | 5 | 40 | 0.427 | NOTE 5 |
| 16 | 160 | 5 | 40 | 0.473 | NOTE 5 |
| 18 | 200 | 4 | PACKING COLUMN (Dixon) | 0.932 | NOTE 5 |
| 19 | NOTE 1 | 5 | 60 | 0.275 | NOTE 5 |
| 20 | NOTE 1 | 5 | 60 | 0.258 | NOTE 5 |
| 21 | NOTE 1 | 5 | 60 | 0.258 | NOTE 5 |
| 22 | 250 | 3 | PACKING COLUMN (Raschig) | 0.392 | NOTE 5 |
| 23 | NOTE 2 | NOTE 2 | NOTE 2 | 0.532 | NOTE 5 |
| 24 | NOTE 3 | NOTE 3 | 42 | NOTE 4 | NOTE 5 |
| 25 | NOTE 3 | NOTE 3 | 30 | 3750 | NOTE 5 |
| 26 | 200 | 15 | PACKING COLUMN (BX) | 0.313 | NOTE 5 |

NOTE 1:
OLDERSHAW DISTILLATION COLUMN.
NOTE 2:
NO DESCRIPTION WHATSOEVER DEFINING DISTILLATION COLUMN.
NOTE 3:
ONLY DESCRIPTION DEFINING DISTILLATION COLUMN IS NUMBER OF STAGES.

TABLE 1-continued

| PATENT DOCUMENT | H: cm | D: cm | NO. STAGES: n | P: kg/hr | T: hr |
|---|---|---|---|---|---|

NOTE 4:
NO DESCRIPTION WHATSOEVER OF PRODUCED AMOUNT.
NOTE 5:
NO DESCRIPTION WHATSOEVER REGARDING STABLE PRODUCTION FOR PROLONGED PERIOD OF TIME.

Note that Patent Document 25 (Japanese Patent Application Laid-Open No. 2003-300936) (paragraph 0060) describes that "The present example uses the same process flow as for the preferred mode shown in FIG. 1 described above, and was carried out with the object of operating a commercial scale apparatus for producing dimethyl carbonate and ethylene glycol through transesterification by a catalytic conversion reaction between ethylene carbonate and methanol. It should be noted that the following numerical values in the present example can be adequately used in the operation of an actual apparatus", and as that example it is stated that 3750 kg/hr of dimethyl carbonate was specifically produced. The scale described in that example corresponds to an annual production of 30,000 tons or more, and hence this implies that at the time of the filing of the patent application for Patent Document 25 (Japanese Patent Application Laid-Open No. 2003-300936) (Apr. 9, 2002), operation of the world's first large scale commercial plant using this process had been carried out. However, even at the time of filing the present application, there is not the above fact at all. Moreover, in the example of Patent Document 25 (Japanese Patent Application Laid-Open No. 2003-300936), exactly the same value as the theoretically calculated value is stated for the produced amount of dimethyl carbonate, but the yield for ethylene glycol is approximately 85.6%, and the selectivity is approximately 88.4%, and hence it cannot really be said that a high yield and high selectivity have been attained. In particular, the low selectivity indicates that this process has a fatal drawback as an industrial production process. (Note also that Patent Document 25 (Japanese Patent Application Laid-Open No. 2003-300936) was deemed to have been withdrawn on Jul. 26, 2005 due to examination not having been requested).

With the reactive distillation method, there are very many causes of fluctuation such as composition variation due to reaction and composition variation due to distillation in the distillation column, and temperature variation and pressure variation in the column, and hence continuing stable operation for a prolonged period of time is accompanied by many difficulties, and in particular these difficulties are further increased in the case of handling large amounts. To continue mass production of the dialkyl carbonates and the diols using the reactive distillation method stably for a prolonged period of time while maintaining high yields and high selectivities for the dialkyl carbonates and the diols, the reactive distillation apparatus must be cleverly devised. However, the only description of continuous stable production for a prolonged period of time with the reactive distillation method proposed hitherto has been the 200 to 400 hours in Patent Document 12 (Japanese Patent Application Laid-Open No. H4-198141) and Patent Document 13 (Japanese Patent Application Laid-Open No. H4-230243).

DISCLOSURE OF INVENTION

Problems to be Solved by the Invention

It is an object of the present invention to provide, for the case of producing dialkyl carbonates and diols industrially in large amounts (e.g. not less than 2 ton/hr for the dialkyl carbonates, and not less than 1.3 ton/hr for the diols) through a reactive distillation system of taking a cyclic carbonate and an aliphatic monohydric alcohol as starting materials, continuously feeding the starting materials into a continuous multi-stage distillation column in which a catalyst is present, and carrying out reaction and distillation simultaneously in the column, a specific process in which the dialkyl carbonates and the diols can be produced with high selectivity and high productivity stably for a prolonged period of time (e.g. not less than 1000 hours, preferably not less than 3000 hours, more preferably not less than 5000 hours).

Means for Solving the Problems

Since the present inventors first disclosed a process for continuously producing the dialkyl carbonates and the diols using the continuous multi-stage distillation column, there have been many proposals regarding improving this process. However, these have been on a small scale and short operating time laboratory level, and there have been no disclosures whatsoever on a specific process or apparatus enabling mass production on an industrial scale stably for a prolonged period of time based on findings obtained through actual implementation. The present inventors have thus carried out studies aimed at discovering a specific process enabling the dialkyl carbonates and the diols to be produced on an industrial scale of, for example, not less than 2 ton/hr for the dialkyl carbonates and not less than 1.3 ton/hr for the diols stably for a prolonged period of time with high selectivity and high productivity. As a result, the present inventors have reached to the present invention.

That is, according to the first aspect of the present invention, there are provided:

1. a process for industrially producing a dialkyl carbonate and a diol in which the dialkyl carbonate and the diol are continuously produced through a reactive distillation system of taking a cyclic carbonate and an aliphatic monohydric alcohol as starting materials, comprising the steps of:

continuously feeding the starting materials into a continuous multi-stage distillation column in which a catalyst is present;

carrying out reaction and distillation simultaneously in said column;

continuously withdrawing a low boiling point reaction mixture containing the produced dialkyl carbonate from an upper portion of the column in a gaseous form; and continuously withdrawing a high boiling point reaction mixture containing the diol from a lower portion of the column in a liquid form, wherein (a) said continuous multi-stage distillation column comprises a structure having a cylindrical trunk portion having a length L (cm) and an inside diameter D (cm) and having thereinside an internal with a number of stages n, and comprises a gas outlet having an inside diameter $d_1$ (cm) at a top of the column or in the upper portion of the column near to the top, a liquid outlet having an inside diameter $d_2$ (cm) at a bottom of the column or in the lower portion of the column near to the bottom, at least one first inlet provided in the upper portion and/or a middle portion of the column below the gas outlet, and at least one second inlet provided in the middle portion and/or the lower portion of the column above the liquid outlet, wherein (1) the length L (cm) satisfies the formula (1);

$$2100 \leq L \leq 8000 \tag{1},$$

(2) the inside diameter D (cm) of the column satisfies the formula (2);

$$180 \leq D \leq 2000 \tag{2},$$

(3) a ratio of the length L (cm) to the inside diameter D (cm) of the column satisfies the formula (3);

$$4 \leq L/D \leq 40 \tag{3},$$

(4) the number of stages n satisfies the formula (4);

$$10 \leq n \leq 120 \tag{4},$$

(5) a ratio of the inside diameter D (cm) of the column to the inside diameter $d_1$ (cm) of the gas outlet satisfies the formula (5);

$$3 \leq D/d_1 \leq 20 \tag{5, and}$$

(6) a ratio of the inside diameter D (cm) of the column to the inside diameter $d_2$ (cm) of the liquid outlet satisfies the formula (6);

$$5 \leq D/d_2 \leq 30 \tag{6},$$

2. the process according to item 1, wherein the produced amount of the dialkyl carbonate is not less than 2 ton/hr, 3. the process according to item 1 or 2, wherein a produced amount of the diol is not less than 1.3 ton/hr, 4. the process according to any one of items 1 to 3, wherein said $d_1$ and said $d_2$ satisfy the formula (7);

$$1 \leq d_1/d_2 \leq 5 \tag{7},$$

5. the process according to any one of items 1 to 4, wherein L, D, L/D, n, $D/d_1$, and $D/d_2$ for said continuous multi-stage distillation column satisfy the following formulae; $2300 \leq L \leq 6000$, $200 \leq D \leq 1000$, $5 \leq L/D \leq 30$, $30 \leq n \leq 100$, $4 \leq D/d_1 \leq 15$, and $7 \leq D/d_2 \leq 25$, respectively, 6. the process according to any one of items 1 to 5, wherein L, D, L/D, n, $D/d_1$, and $D/d_2$ for said continuous multi-stage distillation column satisfy the following formulae; $2500 \leq L \leq 5000$, $210 \leq D \leq 800$, $7 \leq L/D \leq 20$, $40 \leq n \leq 90$, $5 \leq D/d_1 \leq 13$, and $9 \leq D/d_2 \leq 20$, respectively, 7. the process according to any one of items 1 to 6, wherein said continuous multi-stage distillation column is a distillation column having a tray and/or packing as said internal, 8. the process according to item 7, wherein said continuous multi-stage distillation column is a plate type distillation column having a tray as said internal, 9. the process according to item 7 or 8, wherein said tray is a sieve tray having a sieve portion and a downcomer portion, 10. the process according to item 9, wherein the sieve trays has 100 to 1000 holes/m² in the sieve portion thereof, 11. the process according to item 9 or 10, wherein a cross-sectional area per hole of the sieve tray is in a range of from 0.5 to 5 cm².

In addition, according to the second aspect of the present invention, there are provided:

12. a continuous multi-stage distillation column for carrying out transesterification between a cyclic carbonate and an aliphatic monohydric alcohol and distillation, the continuous multi-stage distillation column comprising:

a cylindrical trunk portion having a length L (cm) and an inside diameter D (cm);

an internal having a number of stages n provided inside said trunk portion;

a gas outlet having an inside diameter $d_1$ (cm) provided at a top of said column or in an upper portion of said column near to the top;

a liquid outlet having an inside diameter $d_2$ (cm) provided at a bottom of said column or in a lower portion of said column near to the bottom;

at least one first inlet provided in the upper portion and/or a middle portion of said column below said gas outlet; and at least one second inlet provided in the middle portion and/or the lower portion of said column above said liquid outlet; wherein, (1) a length L (cm) satisfies the formula (1);

$$2100 \leq L \leq 8000 \quad (1),$$

(2) an inside diameter D (cm) of the column satisfies the formula (2);

$$180 \leq D \leq 2000 \quad (2),$$

(3) a ratio of the length L (cm) to the inside diameter D (cm) of the column satisfies the formula (3);

$$4 \leq L/D \leq 40 \quad (3),$$

(4) the number of stages n satisfies the formula (4);

$$10 \leq n \leq 120 \quad (4),$$

(5) a ratio of the inside diameter D (cm) of the column to the inside diameter $d_1$ (cm) of the gas outlet satisfies the formula (5);

$$3 \leq D/d_1 \leq 20 \quad (5), \text{ and}$$

(6) a ratio of the inside diameter D (cm) of the column to the inside diameter $d_2$ (cm) of the liquid outlet satisfies the formula (6):

$$5 \leq D/d_2 \leq 30 \quad (6),$$

13. the continuous multi-stage distillation column according to item 12, wherein $d_1$ and $d_2$ satisfy the formula (7);

$$1 \leq d_1/d_2 \leq 5 \quad (7),$$

14. the continuous multi-stage distillation column according to item 12 or 13, wherein L, D, L/D, n, $D/d_1$, and $D/d_2$ for said continuous multi-stage distillation column satisfy, respectively, $2300 \leq L \leq 6000$, $200 \leq D \leq 1000$, $5 \leq L/D \leq 30$, $30 \leq n \leq 100$, $4 \leq D/d_1 \leq 15$, and $7 \leq D/d_2 \leq 25$, 15. the continuous multi-stage distillation column according to any one of items 12 to 14, wherein L, D, L/D, n, $D/d_1$, and $D/d_2$ for said continuous multi-stage distillation column satisfy, respectively, $2500 \leq L \leq 5000$, $210 \leq D \leq 800$, $7 \leq L/D \leq 20$, $40 \leq n \leq 90$, $5 \leq D/d_1 \leq 13$, and $9 \leq D/d_2 \leq 20$, 16. the continuous multi-stage distillation column according to any one of items 12 to 15, wherein said continuous multi-stage distillation column is a distillation column having a tray and/or packing as the internal, 17. the continuous multi-stage distillation column according to item 16, wherein said continuous multi-stage distillation column is a plate type distillation column having trays as the internal, 18. the continuous multi-stage distillation column according to item 16 or 17, wherein said tray is a sieve tray having a sieve portion and a downcomer portion, 19. the continuous multi-stage distillation column according to item 18, wherein said sieve tray has 100 to 1000 holes/m² in the sieve portion thereof, 20. the continuous multi-stage distillation column according to item 18 or 19, wherein a cross-sectional area per hole of the sieve tray is in a range of from 0.5 to 5 cm².

ADVANTAGEOUS EFFECTS OF THE INVENTION

It has been discovered that by implementing the present invention, the dialkyl carbonates and the diols can be produced each with a high selectivity of not less than 95%, preferably not less than 97%, more preferably not less than 99%, on an industrial scale of not less than 2 ton/hr, preferably not less than 3 ton/hr, more preferably not less than 4 ton/hr, for the dialkyl carbonates, and not less than 1.3 ton/hr, preferably not less than 1.95 ton/hr, more preferably not less than 2.6 ton 1 hr, for the diols, stably for a prolonged period of time of not less than 1000 hours, preferably not less than 3000 hours, more preferably not less than 5000 hours, from the cyclic carbonate and the aliphatic monohydric alcohol.

DESCRIPTION OF REFERENCE NUMERALS

Figure 1:
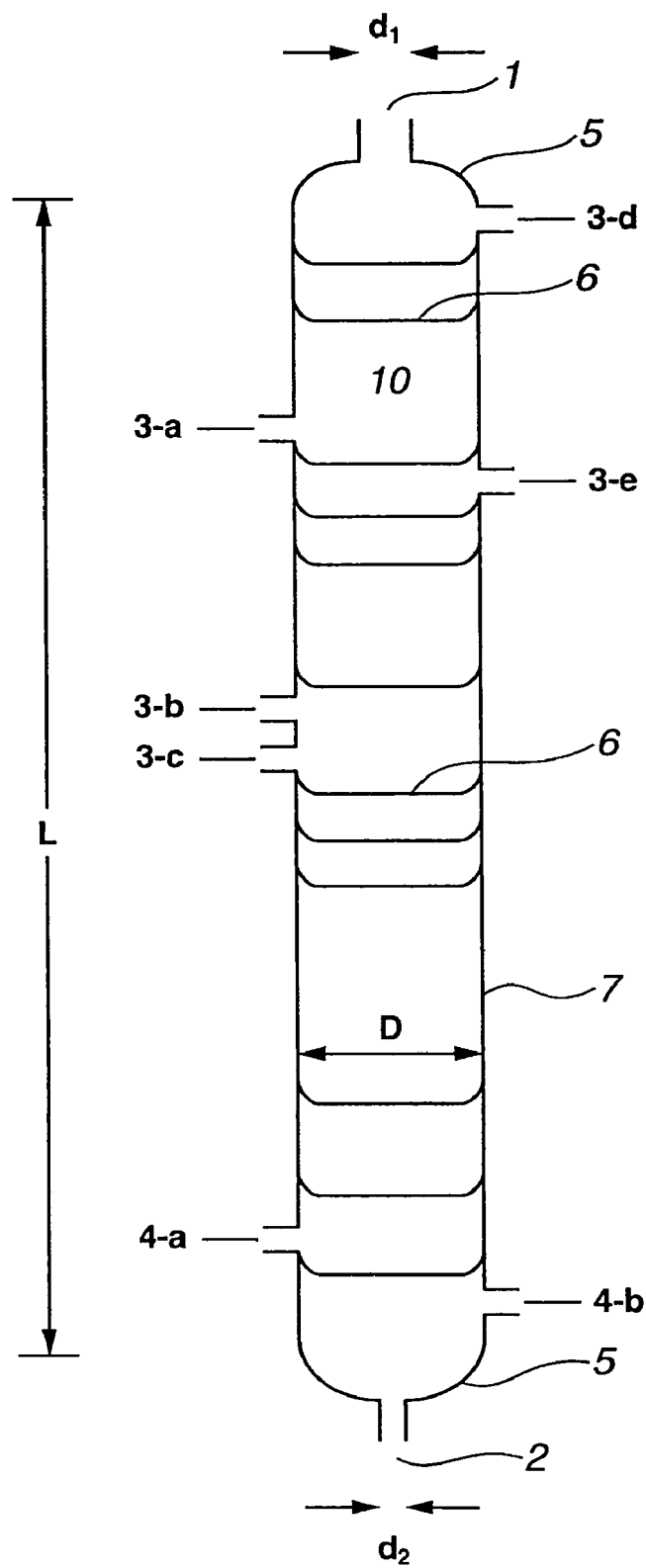
FIG. 1 shows an example of schematic drawing of the continuous multi-stage distillation column for carrying out the present invention, the distillation column having internals (in FIG. 1, tray stages are shown schematically) provided inside a trunk portion thereof.

1: gas outlet; 2: liquid outlet; 3-*a* to 3-*e*: inlet; 4-*a* to 4-*b*: inlet; 5: end plate; 6: internal; 7: trunk portion; 10: continuous multi-stage distillation column; L: length of trunk portion (cm); D: inside diameter of trunk portion (cm); $d_1$: inside diameter of gas outlet; $d_2$: inside diameter of liquid outlet (cm).

BEST MODE FOR CARRYING OUT THE INVENTION

In the following, the present invention is described in detail.

The reaction of the present invention is a reversible equilibrium transesterification reaction represented by following general formula (I) in which a dialkyl carbonate (C) and a diol (D) are produced from a cyclic carbonate (A) and an aliphatic monohydric alcohol (B);

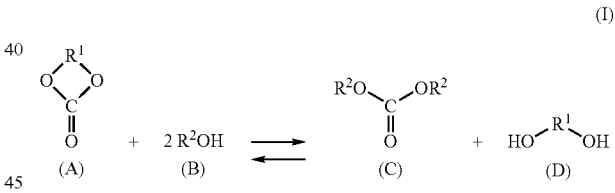

(I)

wherein $R^1$ represents a bivalent group —$(CH_2)_m$— (m is an integer from 2 to 6), one or more of the hydrogens thereof being optionally substituted with an alkyl group or an aryl group having 1 to 10 carbon atoms. Moreover, $R^2$ represents a monovalent aliphatic group having 1 to 12 carbon atoms, one or more of the hydrogens thereof being optionally substituted with an alkyl group or an aryl group having 1 to 10 carbon atoms.

The cyclic carbonate used as a starting material in the present invention is a compound represented by (A) in formula (1). Examples of the cyclic carbonate include alkylene carbonates such as ethylene carbonate or propylene carbonate; or 1,3-dioxacyclohexa-2-one, 1,3-dioxacyclohepta-2-one, or the like, ethylene carbonate or propylene carbonate being preferably used due to ease of procurement and so on, and ethylene carbonate being more preferably used.

Moreover, the aliphatic monohydric alcohol used as the other starting material is a compound represented by (B) in formula (I). An aliphatic monohydric alcohol having a lower boiling point than the diol produced is used. Although possibly varying depending on the type of the cyclic carbonate used, examples of the alipharic monohydric alcohol include methanol, ethanol, propanol (isomers), allyl alcohol, butanol (isomers), 3-buten-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers), and so on. Furthermore, these aliphatic monohydric alcohols may be substituted with substituents such as halogens, lower alkoxy groups, cyano groups, alkoxycarbonyl groups, aryloxycarbonyl groups, acyloxy groups, and nitro groups.

Of such aliphatic monohydric alcohols, ones preferably used are alcohols having 1 to 6 carbon atoms, more preferably alcohols having 1 to 4 carbon atoms, i.e. methanol, ethanol, propanol (isomers), and butanol (isomers). In the case of using ethylene carbonate or propylene carbonate as the cyclic carbonate, preferable examples of the aliphatic monohydric alcohols include methanol and ethanol, methanol being more preferable.

In the process of the present invention, a catalyst is made to be present in the reactive distillation column. The method of making the catalyst be present may be any method, but in the case, for example, of a homogeneous catalyst that dissolves in the reaction liquid under the reaction conditions, the catalyst can be made to be present in the liquid phase in the reactive distillation column by feeding the catalyst into the reactive distillation column continuously, or in the case of a heterogeneous catalyst that does not dissolve in the reaction liquid under the reaction conditions, the catalyst can be made to be present in the reaction system by disposing the catalyst as a solid in the reactive distillation column; these methods may also be used in combination.

In the case that a homogeneous catalyst is continuously fed into the reactive distillation column, the homogeneous catalyst may be fed in together with the cyclic carbonate and/or the aliphatic monohydric alcohol, or may be fed in at a different position to the starting materials. The reaction actually proceeds in the distillation column in a region below the position at which the catalyst is fed in, and hence it is preferable to feed the catalyst into a region between the top of the column and the position(s) at which the starting materials are fed in. The catalyst must be present in at least 5 stages, preferably at least 7 stages, more preferably at least 10 stages.

Moreover, in the case of using the heterogeneous solid catalyst, the catalyst must be present in at least 5 stages, preferably at least 7 stages, more preferably at least 10 stages. A solid catalyst that also has an effect as a packing in the distillation column may be used.

As the catalyst used in the present invention, any of various catalysts known from hitherto can be used. Examples of the catalyst include:

alkali metals and alkaline earth metals such as lithium, sodium, potassium, rubidium, cesium, magnesium, calcium, strontium, and barium;

basic compounds such as hydrides, hydroxides, alkoxides, aryloxides, amides or the like of alkali metals and alkaline earth metals;

basic compounds such as carbonates, bicarbonates, organic acid salts or the like of alkali metals and alkaline earth metals;

tertiary amines such as triethylamine, tributylamine, trihexylamine, and benzyldiethylamine or the like;

nitrogen-containing heteroaromatic compounds such as N-alkylpyrroles, N-alkylindoles, oxazoles, N-alkylimidazoles, N-alkylpyrazoles, oxadiazoles, pyridine, alkylpyridines, quinoline, alkylquinolines, isoquinoline, alkylisoquinolines, acridine, alkylacridines, phenanthroline, alkylphenanthrolines, pyrimidine, alkylpyrimidines, pyrazine, alkylpyrazines, triazines, alkyltriazines or the like;

cyclic amidines such as diazabicycloundecene (DBU), diazabicyclononene (DBN) or the like;

thallium compounds such as thallium oxide, thallium halides, thallium hydroxide, thallium carbonate, thallium nitrate, thallium sulfate, thallium organic acid salts or the like;

tin compounds such as tributylmethoxytin, tributylethoxytin, dibutyldimethoxytin, diethyldiethoxytin, dibutyldiethoxytin, dibutylphenoxytin, diphenylmethoxytin, dibutyltin acetate, tributyltin chloride, tin 2-ethylhexanoate or the like;

zinc compounds such as dimethoxyzinc, diethoxyzinc, ethylenedioxyzinc, dibutoxyzinc or the like;

aluminum compounds such as aluminum trimethoxide, aluminum triisopropoxide, aluminum tributoxide or the like;

titanium compounds such as tetramethoxytitanium, tetraethoxytitanium, tetrabutoxytitanium, dichlorodimethoxytitanium, tetraisopropoxytitanium, titanium acetate, titanium acetylacetonate or the like;

phosphorus compounds such as trimethylphosphine, triethylphosphine, tributylphosphine, triphenylphosphine, tributylmethylphosphonium halides, trioctylbutylphosphonium halides, triphenylmethylphosphonium halides or the like;

zirconium compounds such as zirconium halides, zirconium acetylacetonate, zirconium alkoxides, zirconium acetate or the like;

lead and lead-containing compounds, for example lead oxides such as $PbO$, $PbO_2$, $Pb_3O_2$ or the like;

lead sulfides such as $PbS$, $Pb_2S_3$, $PbS_2$ or the like;

lead hydroxides such as $Pb(OH)_2$, $Pb_3O_2(OH)_2$, $Pb_2[PbO_2(OH)_2]$, $Pb_2O(OH)_2$ or the like;

plumbites such as $Na_2PbO_2$, $K_2PbO_2$, $NaHPbO_2$, $KHPbO_2$ or the like;

plumbates such as $Na_2PbO_3$, $Na_2H_2PbO_4$, $K_2PbO_3$, $K_2[Pb(OH)_6]$, $K_4PbO_4$, $Ca_2PbO_4$, $CaPbO_3$ or the like;

lead carbonates and basic salts thereof such as $PbCO_3$, $2PbCO_3.Pb(OH)_2$ or the like;

alkoxylead compounds and aryloxylead compounds such as $Pb(OCH_3)_2$, $(CH_3O)Pb(OPh)$, $Pb(OPh)_2$ or the like;

lead salts of organic acids, and carbonates and basic salts thereof, such as $Pb(OCOCH_3)_2$, $Pb(OCOCH_3)_4$, $Pb(OCOCH_3)_2.PbO.3H_2O$ or the like;

organolead compounds such as $Bu_4Pb$, $Ph_4Pb$, $Bu_3PbCl$, $Ph_3PbBr$, $Ph_3Pb$ (or $Ph_6Pb_2$), $Bu_3PbOH$, $Ph_2PbO$ or the like (wherein Bu represents a butyl group, and Ph represents a phenyl group);

lead alloys such as Pb—Na, Pb—Ca, Pb—Ba, Pb—Sn, Pb—Sb or the like;

lead minerals such as galena and zinc blende; and hydrates of such lead compounds;

In the case that the compound used dissolves in a starting material of the reaction, the reaction mixture, a reaction by-product or the like, the compound can be used as a homogeneous catalyst, whereas in the case that the compound does not dissolve, the compound can be used as a solid catalyst. Furthermore, it is also preferable to use, as a homogeneous catalyst, a mixture obtained by dissolving a compound as above in a starting material of the reaction, the reaction mixture, a reaction by-product or the like, or by reacting to bring about dissolution.

Furthermore, examples of the catalyst used in the present invention include ion exchangers such as anion exchange resins having tertiary amino groups, ion exchange resins having amide groups, ion exchange resins having at least one type of exchange groups selected from sulfonate groups, carboxylate groups and phosphate groups, and solid strongly basic anion exchangers having quaternary ammonium groups as exchange groups;

solid inorganic compounds such as silica, silica-alumina, silica-magnesia, aluminosilicates, gallium silicate, various zeolites, various metal-exchanged zeolites, and ammonium-exchanged zeolites, and so on.

As a solid catalyst, a particularly preferably used one is a solid strongly basic anion exchanger having quaternary ammonium groups as exchange groups, examples thereof including a strongly basic anion exchange resin having quaternary ammonium groups as exchange groups, a cellulose-based strongly basic anion exchanger having quaternary ammonium groups as exchange groups, and an inorganic carrier supportedtype strongly basic anion exchanger having quaternary ammonium groups as exchange groups. Examples of the strongly basic anion exchange resin having quaternary ammonium groups as exchange groups include a styrene type strongly basic anion exchange resin or the like. A styrene type strongly basic anion exchange resin is a strongly basic anion exchange resin having a copolymer of styrene and divinylbenzene as a parent material, and having quaternary ammonium groups (type I or type II) as exchange groups, and can be schematically represented, for example, by the following formula:

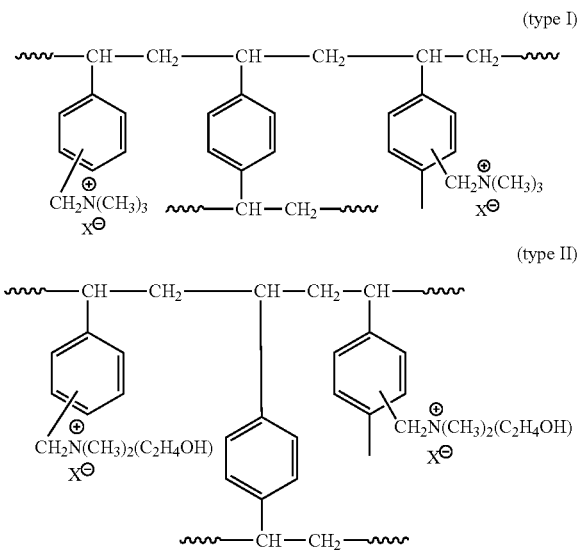

In the above formula, X represents an anion; examples of X include generally at least one type of anion selected from $F^-$, $Cl^-$, $Br^-$, $I^-$, $HCO_3^-$, $CO_3^{2-}$, $CH_3CO_2^-$, $HCO_2^-$, $IO_3^-$, $BrO_3^-$, and $ClO_3^-$, preferably at least one type of anion selected from $Cl^-$, $Br^-$, $HCO_3^-$, and $CO_3^{2-}$. Moreover, examples of the structure of the resin parent material include a gel type structure or a macroreticular (MR) type structure, the MR type being particularly preferable due to the organic solvent resistance being high.

Examples of the cellulose-based strongly basic anion exchanger having quaternary ammonium groups as exchange groups include cellulose having —$OCH_2CH_2NR_3X$ exchange groups obtained by converting some or all of the —OH groups in the cellulose into trialkylaminoethyl groups. Herein, R represents an alkyl group such as methyl, ethyl, propyl, butyl or the like, preferably methyl or ethyl. Moreover, X is defined as above.

The inorganic carrier supported type strongly basic anion exchanger having quaternary ammonium groups as exchange groups that can be used in the present invention means an inorganic carrier that has had —$O(CH_2)_nNR_3X$ quaternary ammonium groups introduced thereto by modifying some or all of the —OH surface hydroxyl groups of the inorganic carrier. Herein, R and X are defined as above, and n is generally an integer from 1 to 6, preferably n=2. Examples of the inorganic carrier include silica, alumina, silica-alumina, titania, zeolite or the like, preferably silica, alumina, or silica-alumina, particularly preferably silica. Any method can be used as the method of modifying the surface hydroxyl groups of the inorganic carrier.

The solid strongly basic anion exchanger having quaternary ammonium groups as exchange groups is commercially available. In this case, the anion exchanger may also be used as the transesterification catalyst after being subjected to ion exchange with a desired anionic species in advance as pretreatment.

Moreover, a solid catalyst comprising a macroreticular or gel-type organic polymer having bonded thereto heterocyclic groups each containing at least one nitrogen atom, or an inorganic carrier having bonded thereto heterocyclic groups each containing at least one nitrogen atom can also be preferably used as the transesterification catalyst. Furthermore, a solid catalyst in which some or all of these nitrogen-containing heterocyclic groups have been converted into a quaternary salt can be similarly used.

Note that a solid catalyst such as an ion exchanger may also act as a packing in the present invention.

The amount of the catalyst used in the present invention varies depending on the type of the catalyst used, but in the case of continuously feeding in a homogeneous catalyst that dissolves in the reaction liquid under the reaction conditions, the amount used is generally in a range of from 0.0001 to 50% by weight, preferably 0.005 to 20% by weight, more preferably 0.01 to 10% by weight, as a proportion of the total weight of the cyclic carbonate and the aliphatic monohydric alcohol fed in as the starting materials. Moreover, in the case of using a solid catalyst installed in the distillation column, the catalyst is preferably used in an amount in a range of from 0.01 to 75 vol %, more preferably 0.05 to 60 vol %, yet more preferably 0.1 to 60 vol %, based on the empty column volume of the distillation column.

There are no particular limitations on the method of continuously feeding the cyclic carbonate and the aliphatic monohydric alcohol into a continuous multi-stage distillation column constituting the reactive distillation column in the present invention; any feeding method may be used so long as the cyclic carbonate and the aliphatic monohydric alcohol can be made to contact the catalyst in a region of at least 5 stages, preferably at least 7 stages, more preferably at least 10 stages, of the distillation column. That is, the cyclic carbonate and the aliphatic monohydric alcohol can be continuously fed in from a required number of inlets in stages of the continuous multi-stage distillation column satisfying the conditions described earlier. Moreover, the cyclic carbonate and the aliphatic monohydric alcohol may be introduced into the same stage of the distillation column, or may be introduced into different stages to one another.

The starting materials are fed continuously into the distillation column in a liquid form, in a gaseous form, or as a mixture of a liquid and a gas. Other than feeding the starting materials into the distillation column in this way, it is also preferable to additionally feed in a gaseous starting material intermittently or continuously from a lower portion of the distillation column. Moreover, another preferable method is one in which the cyclic carbonate is continuously fed in a liquid form or a gas/liquid mixed form into a stage of the distillation column above the stages in which the catalyst is present, and the aliphatic monohydric alcohol is continuously fed in a gaseous form and/or a liquid form into the lower portion of the distillation column. In this case, the cyclic carbonate may of course contain the aliphatic monohydric alcohol.

In the present invention, the starting materials fed in may contain dialkyl carbonate and/or diol being the products. The content thereof is, for the dialkyl carbonate, generally in a range of from 0 to 40% by weight, preferably 0 to 30% by weight, more preferably 0 to 20% by weight, in terms of the percentage by weight of the dialkyl carbonate in the aliphatic monohydric alcohol/dialkyl carbonate mixture, and is, for the diol, generally in a range of from 0 to 10% by weight, preferably 0 to 7% by weight, more preferably 0 to 5% by weight, in terms of the percentage by weight of the diol in the cyclic carbonate/diol mixture.

When carrying out the present reaction industrially, besides fresh cyclic carbonate and/or aliphatic monohydric alcohol newly introduced into the reaction system, materials having the cyclic carbonate and/or the aliphatic monohydric alcohol as a main component thereof recovered from this process and/or another process can also be preferably used for the starting materials. It is an excellent characteristic feature of the present invention that this is possible. An example of another process is a process in which a diaryl carbonate is produced from a dialkyl carbonate and an aromatic monohydroxy compound, the aliphatic monohydric alcohol being by-produced in this process and recovered. The recovered by-produced aliphatic monohydric alcohol generally often contains the dialkyl carbonate, the aromatic monohydroxy compound, an alkyl aryl ether and so on, and may also contain small amounts of an alkyl aryl carbonate, the diaryl carbonate and so on. The by-produced aliphatic monohydric alcohol may be used as is as a starting material in the present invention, or may be used as the starting material after amount of contained material having a higher boiling point than that of the aliphatic monohydric alcohol has been reduced through distillation or the like.

A cyclic carbonate preferably used in the present invention is one produced through reaction between, for example, an alkylene oxide such as ethylene oxide, propylene oxide or styrene oxide and carbon dioxide; a cyclic carbonate containing small amounts of these raw material compounds or the like may be used as a starting material in the present invention.

In the present invention, a ratio between amounts of the cyclic carbonate and the aliphatic monohydric alcohol fed into the reactive distillation column varies according to the type and amount of the transesterification catalyst and the reaction conditions, but a molar ratio of the aliphatic monohydric alcohol to the cyclic carbonate fed in is generally in a range of from 0.01 to 1000 times. To increase the cyclic carbonate conversion, it is preferable to feed in the aliphatic monohydric alcohol in an excess of at least 2 times the number of mols of the cyclic carbonate, but if the amount of the aliphatic monohydric alcohol used is too great, then it is necessary to make the apparatus larger. For such reasons, the molar ratio of the aliphatic monohydric alcohol to the cyclic carbonate is preferably in a range of from 2 to 20, more preferably 3 to 15, yet more preferably 5 to 12. Furthermore, if much unreacted cyclic carbonate remains, then the unreacted cyclic carbonate may react with the produced diol to by-produce oligomers such as a dimer or a trimer, and hence in industrial implementation, it is preferable to reduce the amount of unreacted cyclic carbonate remaining as much as possible. In the process of the present invention, even if the above molar ratio is not more than 10, the cyclic carbonate conversion can be made to be not less than 97%, preferably not less than 98%, more preferably not less than 99%. This is another characteristic feature of the present invention.

In the present invention, preferably not less than 2 ton/hr of the dialkyl carbonate is continuously produced; the minimum amount of the cyclic carbonate continuously fed in to achieve this is generally 2.2 P ton/hr, preferably 2.1 P ton/hr, more preferably 2.0 P ton/hr, based on the amount P (ton/hr) of the dialkyl carbonate to be produced. In a yet more preferable case, this amount can be made to be less than 1.9 P ton/hr.

FIG. 1 shows an example of schematic drawing of the continuous multi-stage distillation column for carrying out the production process according to the present invention. Here, the continuous multi-stage distillation column 10 used in the present invention comprises a structure having a pair of end plates 5 above and below a cylindrical trunk 7 having a length L (cm) and an inside diameter D (cm) and having thereinside an internal with a number of stages n, and further comprises a gas outlet 1 having an inside diameter $d_1$ (cm) at the top of the column or in an upper portion of the column near to the top, a liquid outlet 2 having an inside diameter $d_2$ (cm) at a bottom of the column or in a lower portion of the column near to the column, one or more first inlet 3 (a~e) provided in the upper portion and/or a middle portion of the column below the gas outlet 1, and one or more second inlet 4 (a, b) provided in the middle portion and/or the lower portion of the column above the liquid outlet 2, and moreover must be made to satisfy various conditions so as to be able to carry out not only distillation but also reaction at the same time so as to be able to produce preferably not less than 2 ton 1 hr of the dialkyl carbonate and/or preferably not less than 1.3 ton 1 hr of the diol stably for a prolonged period of time. Note that FIG. 1 is merely one embodiment of the continuous multi-stage distillation column according to the present invention, and hence the arrangement of the tray stages is not limited to that shown in FIG. 1.

The continuous multi-stage distillation column according to the present invention satisfies not only conditions from the perspective of the distillation function, but rather these conditions are combined with conditions required so as make the reaction proceed stably with a high conversion and high selectivity, specifically:

(1) the length L (cm) must satisfy the formula (1);

$$2100 \leq L \leq 8000 \tag{1},$$

(2) the inside diameter D (cm) of the column must satisfy the formula (2);

$$180 \leq D \leq 2000 \tag{2},$$

(3) a ratio of the length L (cm) to the inside diameter D (cm) of the column must satisfy the formula (3);

$$4 \leq L/D \leq 40 \tag{3},$$

(4) the number of stages n must satisfy the formula (4);

$$10 \leq n \leq 120 \tag{4},$$

(5) a ratio of the inside diameter D (cm) of the column to the inside diameter $d_1$ (cm) of the gas outlet must satisfy the formula (5);

$$3 \leq D/d_1 \leq 20 \tag{5, and}$$

(6) a ratio of the inside diameter D (cm) of the column to the inside diameter $d_2$ (cm) of the liquid outlet must satisfy the formula (6);

$$5 \leq D/d_2 \leq 30 \tag{6}$$

Note that the term "the top of the column or the upper portion of the column near to the top" used in the present invention means the portion from the top of the column downward as far as approximately 0.25 L, and the term "the bottom of the column or the lower portion of the column near to the bottom" means the portion from the bottom of the column upward as far as approximately 0.25 L. Here, "L" is as defined above.

It has been discovered that by using the continuous multi-stage distillation column that simultaneously satisfies the formulae (1), (2), (3), (4), (5) and (6), the dialkyl carbonate and the diol can be produced on an industrial scale of preferably not less than 2 ton/hr of the dialkyl carbonate and/or preferably not less than 1.3 ton/hr of the diol with a high conversion, high selectivity, and high productivity stably for a prolonged period of time of, for example, not less than 1000 hours, preferably not less than 3000 hours, more preferably not less than 5000 hours, from the cyclic carbonates and the aliphatic monohydric alcohols. The reason why it has become possible to produce the dialkyl carbonate and the diol on an industrial scale with such excellent effects by implementing the process of the present invention is not clear, but this is supposed to be due to a composite effect brought about when the conditions of the formulae (1) to (6) are combined. Preferable ranges for the respective factors are described below;

If L (cm) is less than 2100, then the conversion decreases and hence it is not possible to attain the desired production amount. Moreover, to keep down the equipment cost while securing the conversion enabling the desired production amount to be attained, L must be made to be not more than 8000. A more preferable range for L (cm) is $2300 \leq L \leq 6000$, with $2500 \leq L \leq 5000$ being yet more preferable.

If D (cm) is less than 180, then it is not possible to attain the desired production amount. Moreover, to keep down the equipment cost while attaining the desired production amount, D must be made to be not more than 2000. A more preferable range for D (cm) is $200 \leq D \leq 1000$, with $210 \leq D \leq 800$ being yet more preferable.

If L/D is less than 4 or greater than 40, then stable operation becomes difficult. In particular, if L/D is greater than 40, then the pressure difference between the top and bottom of the column becomes too great, and hence prolonged stable operation becomes difficult. Moreover, it becomes necessary to increase the temperature in the lower portion of the column, and hence side reactions become liable to occur, bringing about a decrease in the selectivity. A more preferable range for L/D is $5 \leq L/D \leq 30$, with $7 \leq L/D \leq 20$ being yet more preferable.

If n is less than 10, then the conversion decreases and hence it is not possible to attain the desired production amount. Moreover, to keep down the equipment cost while securing the conversion enabling the desired production amount to be attained, n must be made to be not more than 120. Furthermore, if n is greater than 120, then the pressure difference between the top and bottom of the column becomes too great, and hence prolonged stable operation becomes difficult. Moreover, it becomes necessary to increase the temperature in the lower portion of the column, and hence side reactions become liable to occur, bringing about a decrease in the selectivity. A more preferable range for n is $30 \leq n \leq 100$, with $40 \leq n \leq 90$ being yet more preferable.

If $D/d_1$ is less than 3, then the equipment cost becomes high. Moreover, a large amount of a gaseous component is readily released to the outside of the system, and hence stable operation becomes difficult. If $D/d_1$ is greater than 20, then the gaseous component withdrawal amount becomes relatively low, and hence stable operation becomes difficult, and moreover a decrease in the conversion is brought about. A more preferable range for $D/d_1$ is $4 \leq D/d_1 \leq 15$, with $5 \leq D/d_1 \leq 13$ being yet more preferable.

If $D/d_2$ is less than 5, then the equipment cost becomes high. Moreover, the liquid withdrawal amount becomes relatively high, and hence stable operation becomes difficult. If $D/d_2$ is greater than 30, then the flow rate through the liquid outlet and piping becomes excessively fast, and hence erosion becomes liable to occur, bringing about corrosion of the apparatus. A more preferable range for $D/d_2$ is $7 \leq D/d_2 \leq 25$, with $9 \leq D/d_2 \leq 20$ being yet more preferable.

Furthermore, it has been found that in the present invention it is further preferable for $d_1$ and $d_2$ to satisfy the formula (7):

$$1 \leq d_1/d_2 \leq 5 \tag{7}$$

The term "prolonged stable operation" used in the present invention means that the continuous multi-stage distillation column can be operated continuously in a steady state based on the operating conditions with no flooding, clogging of piping, or erosion for not less than 1000 hours, preferably not less than 3000 hours, more preferably not less than 5000 hours, and predetermined amounts of the dialkyl carbonate and the diol can be produced while maintaining the high conversion, high selectivity, and high productivity.

A characteristic feature of the present invention is that the dialkyl carbonate and the diol can be produced stably for a prolonged period of time each with high selectivity and preferably with high productivity for the dialkyl carbonate of not less than 2 ton/hr and high productivity for the diol of not less than 1.3 ton/hr. The dialkyl carbonate and the diol are more preferably produced in an amount of not less than 3 ton/hr and not less than 1.95 ton/hr respectively, yet more preferably not less than 4 ton/hr and not less than 2.6 ton/hr respectively. Moreover, another characteristic feature of the present invention is that in the case that L, D, L/D, n, $D/d_1$, and $D/d_2$ for the continuous multi-stage distillation column satisfy, respectively, $2300 \leq L \leq 6000$, $200 \leq D \leq 1000$, $5 \leq L/D \leq 30$, $30 \leq n \leq 100$, $4 \leq D/d_1 \leq 15$, and $7 \leq D/d_2 \leq 25$, not less than 2.5 ton/hr, preferably not less than 3 ton/hr, more preferably not less than 3.5 ton/hr of the dialkyl carbonate, and not less than 1.6 ton/hr, preferably not less than 1.95 ton 1 hr. more preferably not less than 2.2 ton/hr of the diol can be produced. Furthermore, another characteristic feature of the present invention is that in the case that L, D, L/D, n, $D/d_1$, and $D/d_2$ for the continuous multi-stage distillation column satisfy, respectively, $2500 \leq L \leq 5000$, $210 \leq D \leq 800$, $7 \leq L/D \leq 20$, $40 \leq n \leq 90$, $5 \leq D/d_1 \leq 13$, and $9 \leq D/d_2 \leq 20$, not less than 3 ton/hr, preferably not less than 3.5 ton/hr, more preferably not less than 4 ton/hr of the dialkyl carbonate, and not less than 1.95 ton/hr, preferably not less than 2.2 ton/hr, more preferably not less than 2.6 ton/hr of the diol can be produced.

The term "selectivity" for each of the dialkyl carbonate and the diol in the present invention is based on the cyclic carbonate reacted. In the present invention, a high selectivity of not less than 95% can generally be attained, preferably not less than 97%, more preferably not less than 99%. Moreover, the term "conversion" in the present invention generally indicates the cyclic carbonate conversion, in the present invention it being possible to make the cyclic carbonate conversion be not less than 95%, preferably not less than 97%, more preferably not less than 99%, yet more preferably not less than 99.5%, still more preferably not less than 99.9%. It is one of the excellent characteristic features of the present invention that a high conversion can be maintained while maintaining high selectivity in this way.

The continuous multi-stage distillation column used in the present invention is preferably a distillation column having a tray and/or packing as an internal. The term "internal" used in the present invention means the parts in the distillation column where gas and liquid are actually brought into contact with one another. Examples of the trays include a bubble-cap tray, a sieve tray, a valve tray, a counterflow tray, a Superfrac tray, a Maxfrac tray, or the like. Moreover, in the present invention, the multi-stage distillation column having both a tray portion and a portion packed with packings in part of the tray stage portion can also be used. Examples of the packings include irregular packings such as a Raschig ring, a Lessing ring, a Pall ring, a Berl saddle, an Intalox saddle, a Dixon packing, a McMahon packing or Heli-Pak, or regular packings such as Mellapak, Gempak, TECHNO-PACK, FLEXI-PAK, a Sulzer packing, a Goodroll packing or Glitschgrid. Furthermore, the term "number of stages n of the internals" used in the present invention means the number of trays in the case of trays, and the theoretical number of stages in the case of packings.

For the reaction between the cyclic carbonate and the aliphatic monohydric alcohol in the present invention, it has been discovered that the high conversion, high selectivity, and high productivity can be attained using a plate type continuous multi-stage distillation column and/or a packed column type continuous multi-stage distillation column in which the internals comprise the trays and/or the packings having a predetermined number of stages, but the plate type distillation column in which the internals are trays is preferable. Furthermore, it has been discovered that sieve trays each having a sieve portion and a downcomer portion are particularly good as the trays in terms of the relationship between performance and equipment cost. It has also been discovered that each sieve tray preferably has 100 to 1000 holes/m$^2$ in the sieve portion. A more preferable number of holes is 120 to 900 holes/m$^2$, yet more preferably 150 to 800 holes/m$^2$. Moreover, it has been discovered that the cross-sectional area per hole of each sieve tray is preferably in a range of from 0.5 to 5 cm$^2$. A more preferable cross-sectional area per hole is 0.7 to 4 cm$^2$, yet more preferably 0.9 to 3 cm$^2$. Furthermore, it has been discovered that it is particularly preferable if each sieve tray has 100 to 1000 holes/m$^2$ in the sieve portion, and the cross-sectional area per hole is in a range of from 0.5 to 5 cm$^2$. The number of holes in the sieve portion may be the same for all of the sieve trays, or may differ. It has been shown that by adding the above conditions to the continuous multi-stage distillation column, the object of the present invention can be attained more easily.

When carrying out the present invention, the dialkyl carbonate and the diol are continuously produced by continuously feeding the cyclic carbonate and the aliphatic monohydric alcohol as starting materials into the continuous multi-stage distillation column in which the catalyst is present, carrying out reaction and distillation simultaneously in the column, continuously withdrawing a low boiling point reaction mixture containing the produced dialkyl carbonate from the upper portion of the column in a gaseous form, and continuously withdrawing a high boiling point reaction mixture containing the diol from the lower portion of the column in a liquid form.

Moreover, in the present invention, as the continuous feeding of the starting material cyclic carbonate and aliphatic monohydric alcohol into the continuous multi-stage distillation column, the cyclic carbonate and the aliphatic monohydric alcohol may be fed in as a starting material mixture or separately, in a liquid form and/or a gaseous form, from inlet(s) provided in one place or a plurality of places in the upper portion or the middle portion of the column below the gas outlet in the upper portion of the distillation column. A method in which the cyclic carbonate or the starting material containing a large amount of the cyclic carbonate is fed into the distillation column in a liquid form from inlet(s) in the upper portion or the middle portion of the distillation column, and the aliphatic monohydric alcohol or the starting material containing a large amount of the aliphatic monohydric alcohol is fed into the distillation column in a gaseous form from inlet(s) provided in the middle portion or the lower portion of the column above the liquid outlet in the lower portion of the distillation column is also preferable.

The reaction time for the transesterification reaction carried out in the present invention is considered to equate to the average residence time of the reaction liquid in the continuous multi-stage distillation column. The reaction time varies depending on the form of the internals in the distillation column and the number of stages, the amounts of the starting materials fed in, the type and amount of the catalyst, the reaction conditions, and so on. The reaction time is generally in a range of from 0.1 to 20 hours, preferably 0.5 to 15 hours, more preferably 1 to 10 hours.

The reaction temperature varies depending on the type of the starting material compounds used, and the type and amount of the catalyst. The reaction temperature is generally in a range of from 30 to 300° C. It is preferable to increase the reaction temperature so as to increase the reaction rate. However, if the reaction temperature is too high, then side reactions become liable to occur. The reaction temperature is thus preferably in a range of from 40 to 250° C., more preferably 50 to 200° C., yet more preferably 60 to 150° C. In the present invention, the reactive distillation can be carried out with the column bottom temperature set to not more than 150° C., preferably not more than 130° C., more preferably not more than 110° C., yet more preferably not more than 100° C. An excellent characteristic feature of the present invention is that the high conversion, high selectivity, and high productivity can be attained even with such a low column bottom temperature. Moreover, the reaction pressure varies depending on the type of the starting material compounds used and the composition therebetween, the reaction temperature, and so on. The reaction pressure may be any of a reduced pressure, normal pressure, or an applied pressure, and is generally in a range of from 1 to 2×10$^7$ Pa, preferably 10$^3$ to 10$^7$ Pa, more preferably 10$^4$ to 5×10$^6$ Pa.

The material constituting the continuous multi-stage distillation column used in the present invention is generally a metallic material such as carbon steel or stainless steel. In terms of the quality of the dialkyl carbonate and the diol to be produced, stainless steel is preferable.

EXAMPLES

Following is a more detailed description of the present invention through Examples. However, the present invention is not limited to the following Examples.

Example 1

Continuous Multi-Stage Distillation Column

A continuous multi-stage distillation column as shown in FIG. 1 having L=3300 cm, D=300 cm, L/D=11, n=60, $D/d_1=7.5$, and $D/d_2=12$ was used. In this example, as the internals, sieve trays each having a cross-sectional area per hole in the sieve portion thereof of approximately 1.3 cm$^2$ and a number of holes of approximately 180 to 320/m$^2$ were used.

<Reactive Distillation>

3.27 Ton/hr of ethylene carbonate in a liquid form was continuously introduced into the distillation column from an inlet (3-a) provided at the 55$^{th}$ stage from the bottom. 3.238 Ton/hr of methanol in a gaseous form (containing 8.96% by weight of dimethyl carbonate) and 7.489 ton/hr of methanol in a liquid form (containing 6.66% by weight of dimethyl carbonate) were respectively continuously introduced into the distillation column from inlets (3-b and 3-c) provided at the 31$^{st}$ stage from the bottom. The molar ratio of the starting materials introduced into the distillation column was methanol/ethylene carbonate=8.36.

The catalyst used was obtained by adding 4.8 ton of ethylene glycol to 2.5 ton of KOH (48% by weight aqueous solution), heating to approximately 130° C., gradually reducing the pressure, and carrying out heat treatment for approximately 3 hours at approximately 1300 Pa, so as to produce a homogeneous solution. This catalyst solution was continuously introduced into the distillation column from an inlet (3-e) provided at the 54$^{th}$ stage from the bottom (K concentration: 0.1% by weight based on ethylene carbonate fed in). Reactive distillation was carried out continuously under conditions of a column bottom temperature of 98° C., a column top pressure of approximately 1.118×10$^5$ Pa, and a reflux ratio of 0.42.

It was possible to attain stable steady state operation after 24 hours. A low boiling point reaction mixture withdrawn from the top 1 of the column in a gaseous form was cooled using a heat exchanger and thus turned into a liquid. The liquid low boiling point reaction mixture, which was continuously withdrawn from the distillation column at 10.678 ton/hr, contained 4.129 ton/hr of dimethyl carbonate, and 6.549 ton/hr of methanol. A liquid continuously withdrawn from the bottom 2 of the column at 3.382 ton/hr contained 2.356 ton/hr of ethylene glycol, 1.014 ton/hr of methanol, and 4 kg/hr of unreacted ethylene carbonate. Excluding the dimethyl carbonate contained in the starting material, the actual produced amount of dimethyl carbonate was 3.340 ton/hr, and excluding the ethylene glycol contained in the catalyst solution, the actual produced amount of ethylene glycol was 2.301 ton/hr. The ethylene carbonate conversion was 99.88%, the dimethyl carbonate selectivity was not less than 99.99%, and the ethylene glycol selectivity was not less than 99.99%.

Prolonged continuous operation was carried out under these conditions. After 500 hours, 2000 hours, 4000 hours, 5000 hours, and 6000 hours, the actual produced amounts per hour were 3.340 ton, 3.340 ton, 3.340 ton, 3.340 ton, and 3.340 ton respectively for dimethyl carbonate, and 2.301 ton, 2.301 ton, 2.301 ton, 2.301 ton, and 2.301 ton respectively for ethylene glycol, the ethylene carbonate conversions were respectively 99.90%, 99.89%, 99.89%, 99.88%, and 99.88%, the dimethyl carbonate selectivities were respectively not less than 99.99%, not less than 99.99%, not less than 99.99%, not less than 99.99%, and not less than 99.99%, and the ethylene glycol selectivities were respectively not less than 99.99%, not less than 99.99%, not less than 99.99%, not less than 99.99%, and not less than 99.99%.

Example 2

Reactive distillation was carried out under the following conditions using the same continuous multi-stage distillation column as in Example 1. 2.61 Ton/hr of ethylene carbonate in a liquid form was continuously introduced into the distillation column from the inlet (3-a) provided at the 55$^{th}$ stage from the bottom. 4.233 Ton/hr of methanol in a gaseous form (containing 2.41% by weight of dimethyl carbonate) and 4.227 ton/hr of methanol in a liquid form (containing 1.46% by weight of dimethyl carbonate) were respectively continuously introduced into the distillation column from the inlets (3-b and 3-c) provided at the 31$^{st}$ stage from the bottom. The molar ratio of the starting materials introduced into the distillation column was methanol/ethylene carbonate=8.73. The catalyst was made to be the same as in Example 1, and was continuously fed into the distillation column. Reactive distillation was carried out continuously under conditions of a column bottom temperature of 93° C., a column top pressure of approximately 1.046×10$^5$ Pa, and a reflux ratio of 0.48.

It was possible to attain stable steady state operation after 24 hours. A low boiling point reaction mixture withdrawn from the top 1 of the column in a gaseous form was cooled using a heat exchanger and thus turned into a liquid. The liquid low boiling point reaction mixture, which was continuously withdrawn from the distillation column at 8.17 ton/hr, contained 2.84 ton 1 hr of dimethyl carbonate, and 5.33 ton 1 hr of methanol. A liquid continuously withdrawn from the bottom 2 of the column at 2.937 ton 1 hr contained 1.865 ton/hr of ethylene glycol, 1.062 ton/hr of methanol, and 0.2 kg/hr of unreacted ethylene carbonate. Excluding the dimethyl carbonate contained in the starting material, the actual produced amount of dimethyl carbonate was 2.669 ton 1 hr, and excluding the ethylene glycol contained in the catalyst solution, the actual produced amount of ethylene glycol was 1.839 ton 1 hr. The ethylene carbonate conversion was 99.99%, the dimethyl carbonate selectivity was not less than 99.99%, and the ethylene glycol selectivity was not less than 99.99%.

Prolonged continuous operation was carried out under these conditions. After 1000 hours, 2000 hours, 3000 hours, and 5000 hours, the actual produced amounts per hour were 2.669 ton, 2.669 ton, 2.669 ton, and 2.669 ton respectively for dimethyl carbonate, and 1.839 ton, 1.839 ton, 1.839 ton, and 1.839 ton respectively for ethylene glycol, the ethylene carbonate conversions were respectively 99.99%, 99.99%, 99.99%, and 99.99%, the dimethyl carbonate selectivities were respectively not less than 99.99%, not less than 99.99%, not less than 99.99%, and not less than 99.99%, and the ethylene glycol selectivities were respectively not less than 99.99%, not less than 99.99%, not less than 99.99%, and not less than 99.99%.

Example 3

The continuous multi-stage distillation column as shown in FIG. 1 having L=3300 cm, D=300 cm, L/D=11, n=60, $D/d_1=7.5$, and $D/d_2=12$ was used. In this example, as the internals, sieve trays each having a cross-sectional area per hole in the sieve portion thereof of approximately 1.3 cm$^2$ and a number of holes of approximately 220 to 340/m$^2$ were used.

3.773 Ton/hr of ethylene carbonate in a liquid form was continuously introduced into the distillation column from the inlet (3-a) provided at the 55$^{th}$ stage from the bottom. 3.736 Ton/hr of methanol in a gaseous form (containing 8.97% by weight of dimethyl carbonate) and 8.641 ton/hr of methanol in a liquid form (containing 6.65% by weight of dimethyl carbonate) were respectively continuously introduced into the distillation column from the inlets (3-b and 3-c) provided at the 31$^{st}$ stage from the bottom. The molar ratio of the starting materials introduced into the distillation column was methanol/ethylene carbonate=8.73. The catalyst was made to be the same as in Example 1, and was continuously fed into the distillation column. Reactive distillation was carried out continuously under conditions of a column bottom temperature of 98° C., a column top pressure of approximately 1.118× $10^5$ Pa, and a reflux ratio of 0.42.

It was possible to attain stable steady state operation after 24 hours. A low boiling point reaction mixture withdrawn from the top of the column in a gaseous form was cooled using a heat exchanger and thus turned into a liquid. The liquid low boiling point reaction mixture, which was continuously withdrawn from the distillation column at 12.32 ton/hr, contained 4.764 ton/hr of dimethyl carbonate, and 7.556 ton/hr of methanol. A liquid continuously withdrawn from the bottom of the column at 3.902 ton/hr contained 2.718 ton/hr of ethylene glycol, 1.17 ton/hr of methanol, and 4.6 kg/hr of unreacted ethylene carbonate. Excluding the dimethyl carbonate contained in the starting material, the actual produced amount of dimethyl carbonate was 3.854 ton/hr, and excluding the ethylene glycol contained in the catalyst solution, the actual produced amount of ethylene glycol was 2.655 ton/hr. The ethylene carbonate conversion was 99.88%, the dimethyl carbonate selectivity was not less than 99.99%, and the ethylene glycol selectivity was not less than 99.99%.

Prolonged continuous operation was carried out under these conditions. After 1000 hours, 2000 hours, 3000 hours, and 5000 hours, the actual produced amounts per hour were 3.854 ton, 3.854 ton, 3.854 ton, and 3.854 ton respectively for dimethyl carbonate, and 2.655 ton, 2.655 ton, 2.655 ton, and 2.655 ton respectively for ethylene glycol, the ethylene carbonate conversions were respectively 99.99%, 99.99%, 99.99%, and 99.99%, the dimethyl carbonate selectivities were respectively not less than 99.99%, not less than 99.99%, not less than 99.99%, and not less than 99.99%, and the ethylene glycol selectivities were respectively not less than 99.99%, not less than 99.99%, not less than 99.99%, and not less than 99.99%.

Example 4

The continuous multi-stage distillation column as shown in FIG. 1 having L=3300 cm, D=300 cm, L/D=11, n=60, $D/d_1$=7.5, and $D/d_2$=12 was used. In this example, as the internals, sieve trays each having a cross-sectional area per hole in the sieve portion thereof of approximately 1.3 cm² and a number of holes of approximately 240 to 360/m² were used.

7.546 Ton/hr of ethylene carbonate in a liquid form was continuously introduced into the distillation column from the inlet (3-a) provided at the $55^{th}$ stage from the bottom. 7.742 Ton/hr of methanol in a gaseous form (containing 8.95% by weight of dimethyl carbonate) and 17.282 ton/hr of methanol in a liquid form (containing 6.66% by weight of dimethyl carbonate) were respectively continuously introduced into the distillation column from the inlets (3-b and 3-c) provided at the $31^{st}$ stage from the bottom. The molar ratio of the starting materials introduced into the distillation column was methanol/ethylene carbonate=8.36. The catalyst was made to be the same as in Example 1, and was continuously fed into the distillation column. Reactive distillation was carried out continuously under conditions of a column top temperature of 65° C., a column top pressure of approximately 1.118×$10^5$ Pa, and a reflux ratio of 0.42.

It was possible to attain stable steady state operation after 24 hours. A low boiling point reaction mixture withdrawn from the top 1 of the column in a gaseous form was cooled using a heat exchanger and thus turned into a liquid. The liquid low boiling point reaction mixture, which was continuously withdrawn from the distillation column at 24.641 ton/hr, contained 9.527 ton/hr of dimethyl carbonate, and 15.114 ton/hr of methanol. A liquid continuously withdrawn from the bottom 2 of the column at 7.804 ton/hr contained 5.436 ton/hr of ethylene glycol, 2.34 ton/hr of methanol, and 23 kg/hr of unreacted ethylene carbonate. Excluding the dimethyl carbonate contained in the starting material, the actual produced amount of dimethyl carbonate was 7.708 ton/hr, and excluding the ethylene glycol contained in the catalyst solution, the actual produced amount of ethylene glycol was 5.31 ton/hr. The ethylene carbonate conversion was 99.7%, the dimethyl carbonate selectivity was not less than 99.99%, and the ethylene glycol selectivity was not less than 99.99%.

Prolonged continuous operation was carried out under these conditions. After 1000 hours, the actual produced amount per hour was 7.708 ton for dimethyl carbonate, and 5.31 ton for ethylene glycol, the ethylene carbonate conversion was 99.8%, the dimethyl carbonate selectivity was not less than 99.99%, and the ethylene glycol selectivity was not less than 99.99%.

INDUSTRIAL APPLICABILITY

According to the present invention, it has been discovered that the dialkyl carbonate and the diol can be produced each with a high selectivity of not less than 95%, preferably not less than 97%, more preferably not less than 99%, on an industrial scale of not less than 2 ton/hr, preferably not less than 3 ton/hr, more preferably not less than 4 ton/hr, for the dialkyl carbonate, and not less than 1.3 ton/hr, preferably not less than 1.95 ton/hr, more preferably not less than 2.6 ton/hr, for the diol, stably for a prolonged period of time of not less than 1000 hours, preferably not less than 3000 hours, more preferably not less than 5000 hours, from the cyclic carbonate and the aliphatic monohydric alcohol.

We claim:

1. A process for industrially producing a dialkyl carbonate and a diol in which the dialkyl carbonate and the diol are continuously produced through a reactive distillation system of taking a cyclic carbonate and an aliphatic monohydric alcohol as starting materials, comprising the steps of:
   continuously feeding the starting materials into a continuous multi-stage distillation column in which a catalyst is present;
   carrying out reaction and distillation simultaneously in said column;
   continuously withdrawing a low boiling point reaction mixture containing the produced dialkyl carbonate from an upper portion of the column in a gaseous form; and
   continuously withdrawing a high boiling point reaction mixture containing the diol from a lower portion of the column in a liquid form, wherein
   (a) said continuous multi-stage distillation column comprises a structure having a cylindrical trunk portion having a length L (cm) and an inside diameter D (cm) and having thereinside an internal with a number of stages n, and comprises a gas outlet having an inside diameter $d_1$ (cm) at a top of the column or in the upper portion of the column near to the top, a liquid outlet having an inside diameter $d_2$ (cm) at a bottom of the column or in the lower portion of the column near to the bottom, at least one first inlet provided in the upper portion and/or a middle portion of the column below the gas outlet, and at least one second inlet provided in the middle portion and/or the lower portion of the column above the liquid outlet, wherein (1) the length L (cm) satisfies the formula (1);

$$2100 \leq L \leq 8000 \quad (1),$$

(2) the inside diameter D (cm) of the column satisfies the formula (2);

$$180 \leq D \leq 2000 \quad (2),$$

(3) a ratio of the length L (cm) to the inside diameter D (cm) of the column satisfies the formula (3);

$$4 \leq L/D \leq 40 \quad (3),$$

(4) the number of stages n satisfies the formula (4);

$$10 \leq n \leq 120 \quad (4),$$

(5) a ratio of the inside diameter D (cm) of the column to the inside diameter $d_1$ (cm) of the gas outlet satisfies the formula (5);

$$3 \leq D/d_1 \leq 20 \quad (5), \text{ and}$$

(6) a ratio of the inside diameter D (cm) of the column to the inside diameter $d_2$ (cm) of the liquid outlet satisfies the formula (6);

$$5 \leq D/d_2 \leq 30 \quad (6).$$

2. The process according to claim 1, wherein said $d_1$ and said $d_2$ satisfy the formula (7);

$$1 \leq d_1/d_2 \leq 5 \quad (7).$$

3. The process according to claim 1, wherein L, D, L/D, n, $D/d_1$, and $D/d_2$ for said continuous multi-stage distillation column satisfy the following formulae; $2300 \leq L \leq 6000$, $200 \leq D \leq 1000$, $5 \leq L/D \leq 30$, $30 \leq n \leq 100$, $4 \leq D/d_1 \leq 15$, and $7 \leq D/d_2 \leq 25$, respectively.

4. The process according to claim 1, wherein L, D, L/D, n, $D/d_1$, and $D/d_2$ for said continuous multi-stage distillation column satisfy the following formulae; $2500 \leq L \leq 5000$, $210 \leq D \leq 800$, $7 \leq L/D \leq 20$, $40 \leq n \leq 90$, $5 \leq D/d_1 \leq 13$, and $9 \leq D/d_2 \leq 20$, respectively.

5. The process according to claim 1, wherein said continuous multi-stage distillation column is a distillation column having a tray and/or packing as said internal.

6. The process according to claim 5, wherein said continuous multi-stage distillation column is a plate-type distillation column having a tray as said internal.

7. The process according to claim 5 or 6, wherein said tray is a sieve tray having a sieve portion and a downcomer portion.

8. The process according to claim 7, wherein the sieve trays has 100 to 1000 holes/m² in the sieve portion thereof.

9. The process according to claim 7, wherein a cross-sectional area per hole of the sieve tray is in a range of from 0.5 to 5 cm².

* * * * *